(12) United States Patent
Berger

(10) Patent No.: US 7,976,580 B2
(45) Date of Patent: Jul. 12, 2011

(54) SEMI-CONSTRAINED 1st CARPOMETACARPAL IMPLANT ARTHROPLASTY AND METHOD

(75) Inventor: Richard A. Berger, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 63 days.

(21) Appl. No.: 12/063,794

(22) PCT Filed: Aug. 17, 2006

(86) PCT No.: PCT/US2006/032122
§ 371 (c)(1),
(2), (4) Date: Feb. 14, 2008

(87) PCT Pub. No.: WO2007/022342
PCT Pub. Date: Feb. 22, 2007

(65) Prior Publication Data
US 2008/0221698 A1 Sep. 11, 2008

Related U.S. Application Data

(60) Provisional application No. 60/709,163, filed on Aug. 18, 2005.

(51) Int. Cl.
*A61F 2/42* (2006.01)
(52) U.S. Cl. .................................................. 623/21.13
(58) Field of Classification Search ............... 623/16.11, 623/18.11, 21.11–21.17, 17.14, 19.12, 20.22, 623/22.4, 22.43, 23.4; 606/301
See application file for complete search history.

(56) References Cited

U.S. PATENT DOCUMENTS

| | | | | |
|---|---|---|---|---|
| 4,106,128 A | * | 8/1978 | Greenwald et al. | 623/21.13 |
| 4,276,660 A | * | 7/1981 | Laure | 623/21.16 |
| 4,955,916 A | * | 9/1990 | Carignan et al. | 623/21.16 |
| 5,462,563 A | * | 10/1995 | Shearer et al. | 623/20.11 |
| 5,571,193 A | * | 11/1996 | Kampner | 623/23.57 |
| 5,938,699 A | * | 8/1999 | Campbell | 623/21.13 |
| 6,299,647 B1 | | 10/2001 | Townley | |
| 6,589,284 B1 | | 7/2003 | Silberer | |
| 2005/0033426 A1 | * | 2/2005 | Ogilvie et al. | 623/16.11 |
| 2005/0119757 A1 | | 6/2005 | Hassler et al. | |
| 2006/0235414 A1 | * | 10/2006 | Lim et al. | 606/73 |
| 2006/0241777 A1 | * | 10/2006 | Partin et al. | 623/21.11 |

FOREIGN PATENT DOCUMENTS

DE 4412721 A1 * 10/1994
FR 2661817 A1 * 11/1991

OTHER PUBLICATIONS

International Search Report and Written Opinion issued in PCT/US2006/032122, mailed Jun. 12, 2007.

* cited by examiner

*Primary Examiner* — David Isabella
*Assistant Examiner* — Marcia Hoffman
(74) *Attorney, Agent, or Firm* — Faegre & Benson LLP

(57) ABSTRACT

A first carpometacarpal joint implant. One embodiment of the invention includes proximal and distal components. The proximal component includes a fixation portion for attachment to one or more elements of a patient's distal carpal row, a ball-type joint portion cantilevered off the fixation portion, and a skid having a concave surface opposite the ball-type joint for engaging a patient's scaphoid bone. The distal component has a fixation portion for attachment to a patient's thumb metacarpal, and a socket-type joint portion that cooperates with the ball-type joint portion of the proximal component.

8 Claims, 1 Drawing Sheet

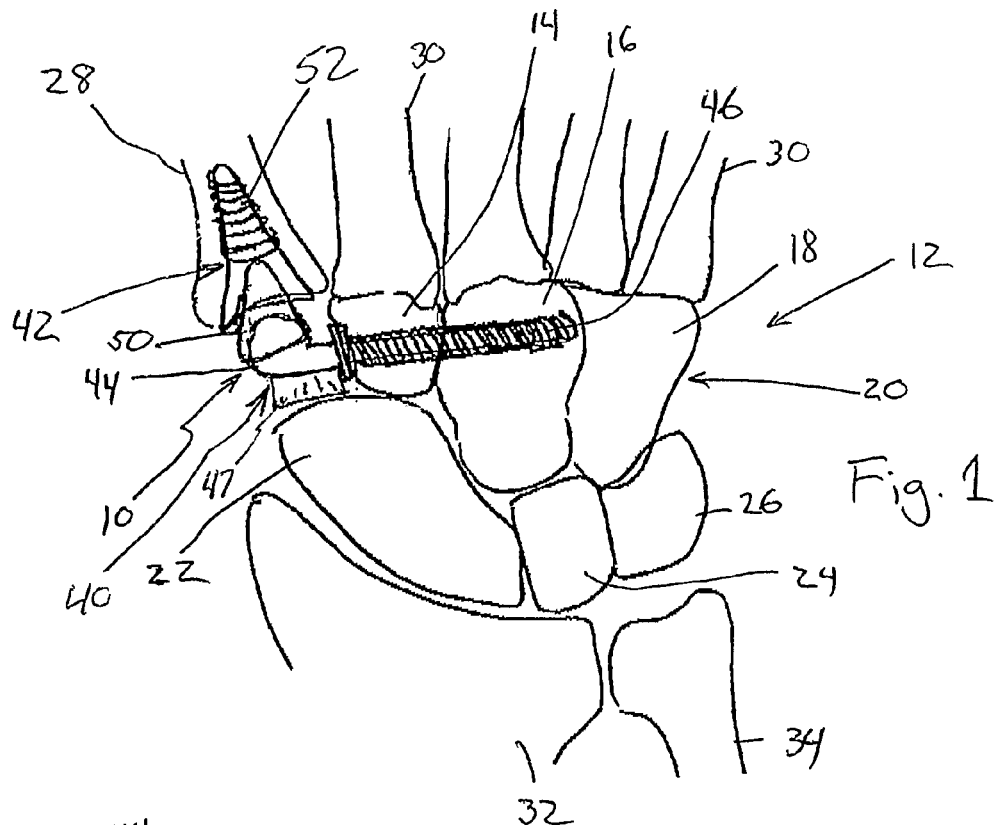
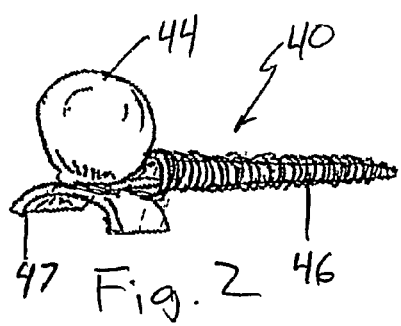
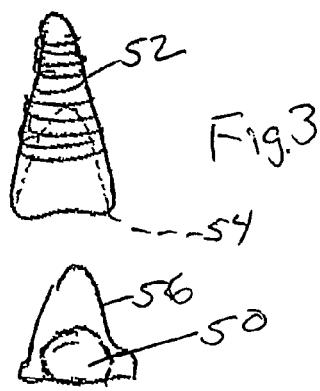
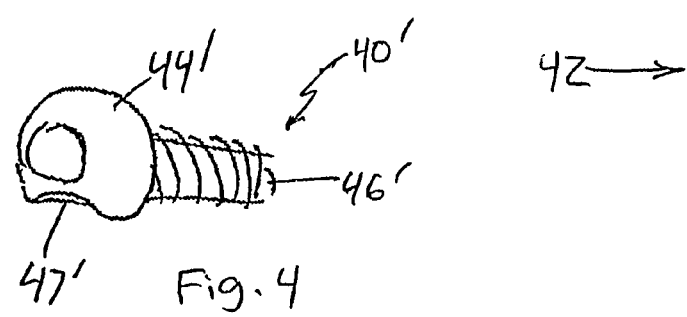

SEMI-CONSTRAINED 1$^{st}$ CARPOMETACARPAL IMPLANT ARTHROPLASTY AND METHOD

REFERENCE TO RELATED APPLICATION

This application claims the benefit of U.S. Provisional Application Ser. No. 60/709,163, filed Aug. 18, 2005, and entitled SEMI-CONSTRAINED 1ST CARPOMETACARPAL IMPLANT ARTHROPLASTY, which is incorporated herein by reference in its entirety.

FIELD OF THE INVENTION

The present invention relates generally to carpometacarpal (CMC) arthroplasty. In particular, the invention is an implant and procedure for theist CMC joint located at the base of the thumb.

BACKGROUND OF THE INVENTION

The joint at the base of the thumb is known as the 1$^{st}$ carpometacarpal (CMC) joint. The bone at the base of the thumb is known as the thumb metacarpal. The trapezium is the bone in the wrist adjacent to the thumb metatacarpal.

Movement of the 1$^{st}$ CMC joint occasionally becomes painful. Reasons for pain of this type include trauma and arthritis. A variety of surgical procedures can be performed to alleviate 1$^{st}$ CMC joint pain. In one surgical procedure, the trapezium is completely removed and the space filled with an interposition graft such as tendon. Another known surgical procedure involves removing only a portion of the trapezium and fixing a spacer to the remaining portion. There remains, however, a continuing need for improved devices and procedures for alleviating pain in the 1$^{st}$ CMC joint.

BRIEF DESCRIPTION OF THE DRAWINGS

FIG. 1 is an illustration of an anterior (palmer) view of the carpal bones of the hand including a ball-and-socket 1$^{st}$ CMC joint implant in accordance with one embodiment of the present invention.

FIG. 2 is a detailed isometric illustration of the proximal or ball component of the implant shown in FIG. 1.

FIG. 3 is a detailed isometric illustration of an alternative embodiment of the proximal or ball component of the implant shown in FIG. 1.

FIG. 4 is an exploded view of the distal or socket component of the implant shown in FIG. 1.

DETAILED DESCRIPTION OF THE PREFERRED EMBODIMENTS

FIG. 1 is an illustration of a 1$^{st}$ carpometacarpal (CMC) joint implant 10 in accordance with one embodiment of the present invention mounted to bones in the hand 12 of a patient. Illustrated wrist bones of the hand 12 include the trapezoid 14, capitate 16 and hamate 18 of the distal carpal row 20, scaphoid 22, lunate 24 and triquetrum 26. Metacarpal 28 of the thumb (the first metacarpal), as well as the metacarpals 30 of the other four fingers are also shown, as is the radius 32 and ulna 34 of the arm. The implant 10 includes a proximal component 40 mounted to and extending from the distal carpal row 20, and a distal component 42 that is mounted to and extends from the thumb metacarpal 28. Proximal component 40 and distal component 42 cooperate as a joint to enable relative movement between metacarpal 28 and trapezoid 14.

As shown in both FIGS. 1 and 2, the proximal component 40 of implant 10 includes a joint portion 44 and a fixation portion 46. Fixation portion 46 is located on the joint portion 44, and in the illustrated embodiment extends from the joint portion. The illustrated embodiment of implant 10 is a ball-and-socket joint, with the joint portion 44 of the proximal component 40 being a generally ball-shaped member having a convex surface portion. A skid 47 is located on one side of the joint portion 44. In the embodiment shown in FIGS. 1 and 2 the skid 47 is a portion of a cylinder wall, opening in a direction opposite the joint portion 44. Fixation portion 46 is an elongated and tapered threaded shaft in the illustrated embodiment. Proximal component 40 can be formed using conventional processes from commercially available and suitable biocompatible materials.

As shown in FIGS. 1 and 3, the distal component 42 of implant 10 also includes a joint portion 50 and a fixation portion 52. Fixation portion 52 is located on the joint portion 50, and in the illustrated embodiment extends from the joint portion. In the illustrated embodiment the joint portion 50 of the distal component 42 is a generally socket-shaped member having a concave surface. The socket-shaped member of the distal component joint portion 50 is sized and shaped to receive and movably cooperate with the ball-shaped member of the proximal component joint portion 44. Fixation portion 52 is an elongated and tapered threaded member in the illustrated embodiment. The distal component 42 is a two-piece member in the illustrated embodiment, with the fixation member 52 having an opening 54 that is sized to receive a cup liner 56 having the joint portion 50. This construction enables the cup liner 56 and joint portion 50 to be fabricated from materials different than those of the fixation portion 52, and optimized for the joint movement function with proximal component joint portion 44. Distal component 42 can be formed using conventional processes from commercially available and suitable biocompatible materials. For example, the cup liner 56 can be formed from high molecular weight polymers.

FIG. 4 is an illustration of an alternative proximal component 40'. The proximal component 40' includes a joint portion 44', a fixation portion 46', and a skid portion 47'. In this embodiment the skid portion 47' is a concave recess in the joint portion 44'. Other than the skid portion 47', proximal component 40 can be similar or substantially the same as proximal component 40 described above.

Implant 10 will typically be implanted into a patient's hand after the trapezium (not shown) has been removed. During the surgical procedure the proximal component 40 is attached to the distal carpal row 20. In particular, the proximal component 40 is attached with the joint portion 44 extending or cantilevered from one or more of the elements of the row 20 and positioned in the space previously occupied by the trapezium. The skid 47, in those embodiments of the invention with this structure, will movably rest on the scaphoid 22 to provide additional support to the proximal component 40. In many patients the joint portion 44 will extend from the trapezoid 14. As shown, the joint portion 44 is generally located and oriented so that the portion that cooperates with the joint portion 50 of the distal component 42 faces or is aligned with the a longitudinal axis of the thumb metacarpal 28. This positional relationship can be described generally as being at a 90° angle with respect to a transverse axis extending through the distal carpal row 20. In the embodiment shown, the fixation portion 46 is secured within a bore extending through both the trapezoid 14 and into capitate 16. In other embodiments (not shown), the fixation portion 46 can be mounted to only the trapezium 14, or to more bones in the distal carpal row 20. Conventional or otherwise known methods can be used to mount the proximal component 40 to the distal carpal row 20.

The distal component 42 is mounted to the thumb metacarpal 28. In the embodiment shown, the fixation portion 52 is secured within a bore extending into the meduallary canal of the metacarpal 28. Conventional or otherwise known methods can be used to mount the distal component 42 to the metacarpal 28.

The jointed implant 10 and procedure of the invention offer important advantages. The implant mimics the natural cantilevered anatomy of the trapezium and its relationship to the distal carpal row bones. The device provides a secure anchor for the proximal component in the bones of the distal carpal row (trapezoid, and possibly capitate and hamate), with a concave articulation with the distal component. The distal component provides spherical proximal articulation with the proximal component. A stable articulating implant is provided between the first metacarpal and the wrist. This stable relationship allows for a functional range of motion and stability to promote strength, and has reduced loosening and subsidence of components over prior art implant structures and methods.

Although the present invention has been described with reference to preferred embodiments, those skilled in the art will recognize that changes can be made in form and detail without departing from the spirit and scope of the invention. In particular, and without limiting the generality of the foregoing statement, other joint-type structures can be implemented by the invention, and other structures and methods can be used to mount the components to the bones.

What is claimed is:

1. A first carpometacarpal ball and socket joint implant for implantation in a patient's wrist following removal of a trapezium from the wrist, including:
    a proximal component having a joint portion, a trapezoid-engaging fixation portion, and a skid, wherein the joint portion includes one of a ball-shaped member having a convex surface and a socket-shaped member having a concave surface, the one of the convex surface of the ball-shaped member and the concave surface of the socket-shaped member of the joint portion extending from the fixation portion at an angle offset from a longitudinal axis of the fixation portion and the fixation portion adapted to penetrate and be fixedly mounted to one or more elements of a patient's distal carpal row including at least a trapezoid to locate and support the joint portion in a fixed cantilevered position with respect to the one or more elements of the patient's distal carpal row in a space previously occupied by the trapezium with the one of the convex surface of the ball-shaped member and the concave surface of the socket-shaped member configured to be aligned with a longitudinal axis of a patient's thumb metacarpal, wherein the skid on the joint portion of the proximal component is configured for movably engaging a patient's scaphoid bone; and a distal component having a joint portion movably mounted to the joint portion of the proximal component, and a metacarpal-engaging fixation portion for attachment to the patient's thumb metacarpal, wherein the joint portion of the distal component includes the other of the ball-shaped member and the socket-shaped member.

2. The implant of claim 1 wherein the joint portion with the socket-shaped member includes a polymer cup slidably mounted to the joint portion.

3. The implant of claim 1 wherein:
    the joint portion of the proximal component includes the ball-shaped member; and
    the joint portion of the distal component includes the socket-shaped member.

4. The implant of claim 3 wherein the joint portion with the socket-shaped member includes a polymer cup slidably mounted to the joint portion.

5. The implant of claim 1 wherein the skid includes a member extending from the proximal component joint portion on a side opposite a side to which the joint portion of the distal component is mounted.

6. The implant of claim 1 wherein the skid includes a recess in the proximal component joint portion on a side opposite a side to which the joint portion of the distal component is mounted.

7. The implant of claim 1 wherein the fixation portion of either or both of the proximal and distal components includes a threaded member.

8. A method for performing $1^{st}$ carpometacarpal implant arthroplasty on a patient, including:
    removing a trapezium;
    penetrating and fixedly mounting a proximal implant component having a joint portion to one or more elements of a distal carpal row including at least a trapezoid, with the joint portion in a fixed cantilevered position with respect to the one or more elements of the distal carpal row by a fixation member off the distal row in a space previously occupied by the trapezium, wherein the proximal component joint portion includes one of a ball-shaped member having a convex surface and a socket-shaped member having a concave surface, and a skid on the joint portion, the one of the convex surface of the ball-shaped member and the concave surface of the socket-shaped member extending from the fixation member at an angle offset from a longitudinal axis of the fixation member and the skid movably engages a patient's scaphoid bone, and wherein the one of the convex surface of the ball-shaped member and the concave surface of the socket-shaped member is aligned with a longitudinal axis of a patient's thumb metacarpal; and
    attaching a distal implant component having a joint portion that movably cooperates with the joint portion of the proximal implant component to the patient's metacarpal, wherein the distal component joint portion includes the other of the ball-shaped member and the socket-shaped member.

* * * * *